United States Patent [19]

Sucholeiki

[11] Patent Number: 5,858,534
[45] Date of Patent: Jan. 12, 1999

[54] METHOD OF MAKING AND USING DERIVATIZED PARAMAGNETIC POLYMER BEADS

[75] Inventor: Irving Sucholeiki, Watertown, Mass.

[73] Assignee: Solid Phase Sciences Corp., Watertown, Mass.

[21] Appl. No.: 749,353

[22] Filed: Sep. 4, 1996

Related U.S. Application Data

[60] Provisional application No. 60/003,233, Sep. 5, 1995.
[51] Int. Cl.$^6$ .................................................... B32B 5/16
[52] U.S. Cl. ....................... 428/407; 436/532; 436/533; 523/202; 523/205; 523/210; 530/334
[58] Field of Search ........................ 252/62.54; 428/407; 523/202, 205, 210; 436/532, 533; 530/334

[56] References Cited

U.S. PATENT DOCUMENTS

| | | | |
|---|---|---|---|
| 4,271,139 | 6/1981 | Hart | 424/1 |
| 4,569,967 | 2/1986 | Kornreich et al. | 525/54.11 |
| 4,638,032 | 1/1987 | Benner | 525/54.11 |
| 4,774,265 | 9/1988 | Ugelstad et al. | 521/55 |
| 4,908,405 | 3/1990 | Bayer et al. | 525/61 |
| 5,202,418 | 4/1993 | Lebl et al. | 530/334 |
| 5,283,079 | 2/1994 | Wang et al. | 427/2 |
| 5,320,944 | 6/1994 | Okada et al. | 435/7.94 |
| 5,639,620 | 6/1997 | Siiman et al. | |

FOREIGN PATENT DOCUMENTS

| | | |
|---|---|---|
| WO 83/03920 | 11/1983 | WIPO . |
| WO 92/04384 A1 | 3/1992 | WIPO . |

OTHER PUBLICATIONS

Fjeld, J.G.; Benestad, H.B.; Stigbrand, T.; Nustad, K. *J. Immunol. Methods* 1988, 109, 1.

Treleaven, J.G.; Gibson, J.; Ugelstad, J.; Rembaum, A.; Philip, T.; Caine, G.C.; Kemshead, J.; *Lancet*, 1984, 14, 70.

Miltenyi, S.; Muller, W.; Weichel, W.; Radbruch, A. *Cytometry*, 1990, 11, 231.

Padmanabhan, R.; Corsico, C.D.; Howard, T.H.; Holter, W.; Fordis, C.M.; Willingham, M.; Bruce, H. *Analytical Biochem.*, 1988, 170, 341.

Regen, S.L. *J. Am. Chem. Soc.* 1974, 96, 5275.

Regen, S.L. *Macromolecules* 1975, 8, 689.

Green, J.; Bradley, K. *Tetrahedron*, 1993, 49, 4141.

Albericio, F., et al.; pp. 271–272.

Hermanson, Greg T., et al., *Immobilized Affinity Ligand Techniques*, 1992, 234–236.

*Primary Examiner*—Melvyn I. Marquis
*Assistant Examiner*—D. Aylward
*Attorney, Agent, or Firm*—Sharon L. Day

[57] ABSTRACT

A solid phase magnetic support having a hydrophilic surface, a method of making the support, and a method of using the support for peptide synthesis are provided. The solid phase magnetic support is synthesized from a starting material which is a magnetic polystyrene polymer bead which has a plurality of polystyrene coated metal oxide particles randomly distributed in a polystyrene matrix having chloromethyl groups. Hydrophilic long chain hydrocarbon spacer arms, such as polyalkylene diamine molecules are coupled with sonication to the chloromethyl groups. Each spacer arm is provided with a terminal amine for linking to a first amino acid. Preferably, the terminal amine on the spacer arm is provided by a low molecular weight linker molecule which can be acid cleaved from the spacer arm. However, the spacer arm may be derivatized and linked to a first amino acid which cannot be acid cleaved from the spacer arm. The inventive support can be used for automated peptide synthesis or as a support for a bound ligand in bioassays. The support is held in place magnetically while the surrounding solution is siphoned off allowing simultaneous separation of the support bound component from the reactants in solution and washing.

20 Claims, 2 Drawing Sheets

METHOD OF MAKING AND USING DERIVATIZED PARAMAGNETIC POLYMER BEADS

This application claims the benefit of U.S. provisional application Ser. No. 60/003,233, filed Sep. 5, 1995.

FIELD OF THE INVENTION

The present invention relates to the synthesis and use of derivatized paramagnetic polymer beads which are rendered hydrophilic, which are stable in organic solvents and which have improved wetting and swelling properties in water. The inventive beads find use in the synthesis of complex organic compounds and in bioassays.

BACKGROUND OF THE INVENTION

Solid-supported organic synthesis has recently entered a renaissance due to the emergence of the field of combinatorial chemistry, aimed at rapidly synthesizing vast libraries of compounds for biological testing (Moos, W. H.; et al., *Annual Reports in Medicinal Chemistry* (Bristol, J. A. editor), 28:315 (1993)). Most of these libraries are produced through solid-supported organic synthesis and consist of peptides or peptide-like compounds (Zuckermann, R. N.; et al., *J. Am. Chem. Soc.*, 114:10646 (1992); Houghten, R. A.; et al., *Nature*, 354:84 (1991)). Some groups have begun to produce chemical libraries that do not rely on the peptide backbone (Lebl, M.; et al., *Int. J. Pept. Protein Res.*, 41:201 (1993); Dewitt, S. H.; et al., *Proc. Natl. Acad. Sci. USA*, 90:6909 (1993)). The major advantage in producing chemical libraries by solid-supported synthesis over traditional solution synthesis is the relative ease in separating starting material from product. This rapid ability to separate staring material from product can also make the library's production through automation that much easier.

However, in the field of solid-supported peptide synthesis, the methods of separation have been filtration and centrifugation. The physical separation of the support from the solubilized components of the reaction mixture has primarily been accomplished by filtration through a glass or polymer filter (Wolfe, H. R.; Wilk R. R., *Peptide Research*, 2:352 (1989); Knapp, D. R.; et al., *Int. J. Peptide Protein Res.*, 42:259 (1993)). Centrifugation has also been used as a means of separation (Anderson, N. G.; et al., J. In *Innovation and Perspectives in Solid Phase Synthesis*, Oxford, In Press (1993); Lebl. M., et al., U.S. Pat. No. 5,202,418). Although filtration has been the method of choice in both solid-phase peptide and nucleotide synthesis, it does have limitations that warrant the development of new approaches. One such limitation is the difficulty of automating the simultaneous washing and filtration of hundreds of small scale solid-phase reactions. Another problem is the tendency for a percentage of the filters to get clogged over time with precipitated reagent which makes the use of filtration in automated procedures less reliable.

Automation of bioassays and organic syntheses is desirable to improve quality control in order to insure uniformity of results. A field that has had some success in automating some of its techniques is immunodiagnostics. Antibody-bound paramagnetic beads can be exposed to a magnetic field to separate antibody-bound antigen from unbound antigen in immunoassays (Okada, M., et al., U.S. Pat. No. 5,320,944; Ugelstad, J., et al., WO 83/03920; Fjeld, J. G., et al., *J. Immunol. Methods*, 109:1 (1988)), each of which is incorporated herein by reference. Assays directly measuring the radiolabeled ligand-protein complex after it has been separate from unbound material are termed radioimmunoassays. Alternatively, in a method termed scintillation proximity assay, the extent of binding is determined by measuring the intensity of fluorescence released when the radiolabel affects a fluorescent molecule bound to another particle (H. Hat; U.S. Pat. No. 4,271,139) incorporated herein by reference. However, the loading capacity of the support systems currently used is limited. Further, non-specific binding of unbound reactants to the support can yield incorrectly elevated values.

Magnetic separation methods have also been applied successfully in cell sorting (Treleaven, J. G.; *Lancet*, 14:70 (1984); Miltenyi, S.; et al.; *Cytometry*, 11:231 (1990); Padmanabhan, R., et al., *Analytical Biochem.*, 170:341 (1988)). A definite advantage that magnetic separation has over simple filtration is the ability to separate out particles in small reaction volumes. As with immunoassays, the loading capacity of the support systems currently used is limited.

Unlike immunodiagnostic and cell sorting technologies, the use of magnetic separation in the field of solid-supported organic chemistry has been slow in coming due to the instability in organic solvents such as dimethylformamide and methylene chloride exhibited by the currently available supports. Upon exposure to these solvents, typical polymer coated magnetic beads dissolve. Silica coated magnetic beads are more stable to these solvents but lack the loading capacity (typically<0.2 mmoles/gram) and acid stability that make them practical for organic synthesis (Benner S. A., U.S. Pat. No. 4,638,032).

One way to increase paramagnetic polymer beds stability in organic solvent is to enhance the levels of cross-linking of the polymer around the magnetite core to make macroporous polymer particles (Ugelstad, J., et al., U.S. Pat. No. 4,774,265; Wang, C. H. J., and Shah, D. O., U.S. Pat. No. 5,283,079), each of which is incorporated herein by reference. A major problem with this approach is that higher levels of cross-linking reduce the extent to which the support expands and contracts and also affects the level of reactivity. Work by Regen using electron spin resonance (ESR) spectroscopy of nitroxide radical probes showed that the bound substrate was more restricted than a substrate dissolved in the swollen particle (Regen, S. L. *J. Am. Chem. Soc.*, 96:5275 (1974); Regen, S. L., *Macromolecules*, 8: 689 (1975)). In addition, Regen provided evidence that with greater cross-linking, which translates to less expansion of the support, the internal viscosity of the solvent increased.

Again looking to the non-magnetic solid-phase support field, one can dramatically enhance the mobility of the bound substrate even with high levels of cross-linking of the support by attaching a long polyethylene glycol (MW= 2000–3000 daltons) spacer arm which acts as a linker between the bound molecule and the support (Bayer, E., and Rapp, W., U.S. Pat. No. 4,908,405; Barany, G., et al., WO 92/04384), each of which is incorporated herein by reference. However, previous methods required multiple, complex reactions to achieve coupling of the spacer arm to the support.

Clearly, what is needed is an organic solvent stable support which can achieve high loading capacities, which is easily manufactured, and which is useful in automated assays and solid phase organic syntheses.

OBJECTIVES

It is an object of the present invention to provide a stable support for bound reactants involved in chemical reactions with unbound reactants in organic solvents which will allow automation of the separation of the reaction products from the reactants remaining in solution. It is also an object of this invention to provide a paramagnetic particle which has a large loading capacity. It is a further object to provide a paramagnetic particle which provides uniform availability of bound reactants to unbound reactants in solution, and which allows a high rate of reaction between the bound and unbound reactants. It is a still further object of this invention to provide haloalkyl derivatized polystyrene paramagnetic beads having a plurality of long chain hydrophilic groups for coupling to reactants.

It is also an object of this invention to provide a process for peptide synthesis in polar organic solvents utilizing the inventive paramagnetic bead. Additionally, it is an object of this invention to provide a process which can be automated for separation of oligomers from reactants utilizing the inventive paramagnetic beads.

It is a further object of this invention to provide a process for ligand binding assays in aqueous solvent utilizing an antibody bound to the surface of the inventive bead.

It is a still further object of this invention to provide a method for synthesizing polystyrene paramagnetic beads, having a hydrophilic coating comprised of a polyalkylene glycol diamine, capable of binding an amino acid, peptide, or protein.

SUMMARY OF THE INVENTION

The invention herein comprises a paramagnetic polystyrene polymer solid-phase support, a method of making the polystyrene solid-phase support, and a method of utilizing the inventive support for peptide synthesis in polar organic solvents or for bioassays. As used herein, a spacer arm (also termed an "arm") is defined as a long chain hydrophilic molecule which will distance the binding site of an amino acid, a peptide or a protein from the polystyrene coated bead. A linker is defined as a low molecular weight organic molecule having a functional reactive group at its first end which is capable of forming an amide bond with the spacer arm, and which can bind an amino acid at its second end. Preferably for organic syntheses, the linker when so bound is acid cleavable at is second end.

Preferably, the inventive paramagnetic support is comprised of a polystyrene paramagnetic bead having diamine polyalkylene glycol groups bound through amination to haloalkyl functionalities on the bead. However, other long chain hydrophilic groups which can be bound through the haloalkyl groups on the bead and which will provide a reactive amine may be utilized. The inventive support provides a bead which is stable in polar organic solvents, can swell or shrink without loss of metal oxide, has a high loading capacity, and provides ease of separation of bead bound reactants from unbound reactants in solution. Due to the hydrophilic nature of the polyalkylene glycol environment formed on/or near the surface of the hydrophobic bead, specificity of loading is achieved.

The paramagnetic solid-phase support is formed by providing a polystyrene bead which is comprised of a plurality of primary polystyrene coated metal oxide particles in a polystyrene matrix; sonicating and heating the bead in the presence of an excess of a hydrophilic long chain hydrocarbon, preferably polyalkylene glycol diamine, to provide a bead having a spacer arm; and attaching a linker to the spacer arm at the terminal alkylamine group. The type of linker utilized is dependent upon whether the bead is to be used as a support for peptide or protein synthesis or as a support for a ligand in an assay system.

When the inventive bead is used for peptide synthesis, preferably the linker has a protected amine site. Once this site is deprotected, it is used for building the peptide by sequential amino acid additions. The beads are magnetically separated from the unreacted components in solution and washed. When the desired peptide or protein is achieved, the peptide is acid cleaved from the linker without need for additional purification.

When the inventive support is to be used in a ligand binding assay, a carboxlyate which is capable of binding a reduced antibody and the terminal alkylamine of the spacer arm on the bead, may be utilized. After coupling of a reduced antibody, a protein, to the linker, the inventive bead-spacer arm-linker-reduced antibody complex ("bead complex") may be introduced into a solution containing a unknown amount of antigen. After allowing time for the bead-spacer arm-linker-reduced antibody complex to bind to the antigen, the bead complex may be magnetically separated from the unbound component sin the solution with little or no non-specific binding and the amount of antigen present may be quantified by known methods.

DETAILED DESCRIPTION OF THE PREFERRED EMBODIMENTS

The present invention provides a paramagnetic polymer bead having a spacer arm which renders the surface of the paramagnetic polymer bead hydrophilic and which is utilized to distant the polymer bead form attached reactants, a method of making the inventive bead, and a method of using the inventive bead for peptide synthesis. The starting material is selected from thermoplastic polymer coated metal oxide particles or beads such as are known in the art and are available from Baxter Laboratories (Deerfield, Ill.), Dynal, Inc. (Lake Success, N.Y.), Rhone Pouonc (France), and SINTEF (Trondheim, Norway). Preferably, the starting material is a paramagnetic polystyrene polymer bead comprised of 1.) a plurality of primary beads or particles, each of which is a polystyrene polymer coated or polymer encapsulated metal oxide which has inducible magnetic properties, and 2.) a mesh or matrix comprised of a polystyrene divinylbenzene polymer resin having less than about 5% divinylbenzene which is capable of swelling or expanding in organic solvent, wherein the primary beads are randomly distributed throughout the matrix. A novel composite magnetic bead of the present invention is comprised of a plurality of encapsulated metal oxide particles, and a microporous polymer resin matrix which has the capacity for functionalization or derivatization. The encapsulated metal oxide particles, herein also referred to as primary beads, have a rigid polymeric coating encapsulating the metal oxide particle. The composite magnetic beads swell in organic solvents such as dimethylformamide and dimethyl sulfoxide without losing their paramagnetic properties and provide a high surface area which can contact the solvent and which can be functionalized to allow binding to the polymeric surface, thereby providing increased capacity for organic synthesis and increased loading capacity for separating a bound component from a component in solution or suspension. These composite magnetic beads are able to withstand high temperatures in highly polar solvents as well as high energy sonication.

As used herein the term "metal oxide particle" refers to any oxide of a metal or metal alloy having paramagnetic or superparamagnetic properties. "Paramagnetic particle" is defined as a metal oxide particle which is susceptible to the application of external magnetic fields, yet is unable to maintain a permanent magnetic domain. The term "rigid" refers to a polymeric coating which is cross linked to the extent that the polymeric coating stabilizes the metal oxide particle within the coating (i.e. the coating essentially does not swell or dissolve) so that the particle remains enclosed therein. The term "microporous" refers to a resinous polymeric matrix which swells or expands in polar organic solvent. The term "load" is used to mean the capacity of the bead for attachment sites useful for functionalization or derivatization.

The primary beads or particles of this invention may be prepared from the raw materials or from metal oxides which are encapsulated by monomers which when crosslinked form rigid, polymeric coatings. Suitable substances which may be incorporated as magnetizable materials, for example, include iron oxides such as magnetite, ferrites of manganese, cobalt, and nickel, hematite and various alloys. Magnetite is the preferred metal oxide. Frequently, metal salts are taught to be converted to metal oxides then either coated with a polymer or adsorbed into a bead comprised of a thermoplastic polymer resin having reducing groups thereon. When starting with metal oxide particles to obtain a hydrophobic primary bead, it is necessary to provide a rigid coating of a thermoplastic polymer derived from vinyl monomers, preferably a cross-linked polystyrene which is capable of binding or being bound by a microporous matrix. Magnetic particles may be formed by procedures shown in Vandenberge, et al., "Preparation and Magnetic Properties of Ultrafine Cobalt Ferrites," *J. of Magnetism and Magnetic Materials,* 15–18: 1117–18 (1980); E. Matjevic, "Monodispersed Metal (Hydrous) Oxides—A Fascinating Field of Colloidal Science,"*Acc. Chem. Res.,* 14: 22–29 (1981), U.S. Pat. Nos. 5,091,206; 4,774,265; 4,554,088; and 4,421,660. Examples of primary beads which may be used in this invention are shown in U.S. Pat. Nos. 5,395,688; 5,318,797; 5,283,079; 5,232,782 5,091,206; 4,965,007; 4,774,265; 4,656,267; 4,490,436; 4,336,183; and 4,421,660, each disclosure of which is incorporated herein by reference. Or, primary beads may be obtained commercially from available hydrophobic or hydrophilic beads which meet the starting requirements of size, sufficient stability of the polymeric coating to swelling in solvents to retain the paramagnetic particle, and ability to adsorb or absorb the vinyl monomer used to form the enmeshing matrix network. Preferably, the primary bead is a hydrophobic, polystyrene encapsulated, paramagnetic bead. Such polystyrene paramagnetic beads are available from Dynal, Inc. (Lake Success, N.Y.), Rhone Poulonc (France), and SINTEF (Trondheim, Norway). The use of toner particles or of magnetic particles having a first coating of an unstable polymer which are further encapsulated to produce an exterior rigid polymeric coating is also contemplated.

Primary particles or beads have an average diameter of about 100 micrometers or less, preferably 1 to 10 micrometers. The primary particles or beads must be capable of participating in a polymerization reaction, preferably as seed particles, with additional monomers which form a microporous thermoplastic polymer mesh or matrix. The rigid polymer coat enclosing the metal oxide must be of a thickness, density, and composition such that it retains the metal oxide therein during and after the polymerization resulting in the final composite bead. An example of one type of rigid polymeric coating is a polystyrene coating formed from a styrene composition having at least a 10% by monomer weight content of divinyl benzene. Further, the coating must not negatively affect the magnetic properties of the enclosed magnetite. The rigid polymeric coating may render the primary particle hydrophobic or hydrophilic. Preferably, the primary beads are hydrophobic due to the properties of the rigid polymeric coating. The encapsulating rigid polymer may be obtained from monomers or combinations of monomers such as a polystyrene, a poly (chloromethyl styrene), a poly(bromo styrene), a poly (methyl methacrylate), or a poly(methyl acrylate). It should be apparent to those skilled in the art that the required coating thickness and the required degree of monomer cross-linking are dependent and thus can be varied relative to one another to achieve the desired result.

Polymerization of the matrix to enmesh the primary beads thus forming the composite beads, occurs in a two phase system, a continuous fluid phase and a dispersed phase, using a method similar to that described in U.S. Pat. No. 5,277,979 (Kielbania, et. al.), the disclosure of which is incorporated herein by reference. The primary beads may be hydrophilic or hydrophobic. When the primary beads are hydrophobic, then the continuous fluid phase is hydrophilic and the dispersed phase is hydrophobic. An aqueous solvent such as water is combined with a dispersant which may also act as an emulsion stabilizer to form the continuous fluid phase. The primary beads and matrix forming monomers are combined in the dispersed phase. Primary beads sized from about 0.05 to about 50.00 um, preferably from about 1 to about 10 um, are used.

The monomers which are suitable for forming the matrix are vinyl monomers such as styrenes, acrylates, methacrylates and the like. Derivatives of these vinyl monomers, for example, methyl acrylate, butyl acrylate, methyl methacrylate, and functionalized derivatives, for example, bromo styrene, chloromethyl styrene, 2-aminoethyl methacrylate, and trimethylammoniumethyl methacrylate, may also be used. Inclusion of a desired percentage of functionalized derivatives eliminates the step of providing functionalized groups after the polymerization has been completed. When the monomer chosen to be added in the dispersed phase has only one vinyl group, it is desirable to include another monomer having more than one vinyl group to facilitate cross-linking. The ratio o various monomers is chosen to provide a final microporous polymer which is cross-linked to the extent of about 1 to 8%.

A polymerization initiator may also be added at about 0.5 to 10% by weight based upon the weight of the total monomer(s) added when the polymeric matrix is formed using a free radical polymerization. The preferred initiators are alkyl and aryl peroxides such as dioctanoyl peroxide and benzoyl peroxide, and nitriles such as azobisisobutyronitrile. Preferably, benzoyl peroxide is used. However, other means of polymerization such as redox or uv irradiation could also be used and at least in the case of UV polymerization, the polymerization initiator could be eliminated or a photoinitiator may be used.

The dispersing agent is preferably added to aid in setting the final composite bead size. Examples of dispersing agents include polymeric dispersants and protective colloids; however, surfactants may also function in this manner. Dispersants include gum arabic, gelatin, cellulose-based compounds, maleic-anhydride-styrene copolymers, and partially hydrolyzed polyvinyl alcohol. Suitable surfactants include sodium lauryl sulfate, sodium dodecylbenzene, sulfonate, and dialkyl succinates. The dispersant is present in an amount of from about 0.1 to about 10 wt. % based upon the weight of the continuous phase solvent.

The diluent is an inert solvent in the matrix-forming monomers can be solubilized. When the primary bead has a hydrophobic encapsulating coat, the diluent preferably is oil-soluble. Examples of preferred diluents useful when the primary bead is hydrophobic and the monomers are selected from the group of styrene monomers include diethylbenzene, toluene, and dichloroethane. The diluent is used at a concentration of up to 150 wt. % based upon the weight of monomer to be polymerized. The diluent chosen may slightly swell the polymeric coating on the primary bead so long as the coating maintains the metal oxide therein.

In the preferred embodiment, styrene monomers, divinyl benzene monomers at about 1 to about 8 weight % of the total monomers, a diluent or solvent for the monomers and hydrophobic primary beads at a weight ratio percent of about 1 to 20%, preferably about 2 to 10% based upon the total weight amount of the monomer(s) added for the polymerization, are combined with a polymerization initiator and an emulsion inhibitor to form the dispersed phase. A continuous fluid phase is formed from purified water and partially hydrolyzed polyvinyl alcohol. A free radical polymerization is initiated when the continuous phase and the dispersed have been thoroughly mixed. The preferred emulsion inhibitor which also may act as an anti-oxidant is sodium nitrite. It should be noted that when methacrylate based monomers are combined to form the polymeric matrix, the addition of an emulsion inhibitor is unnecessary.

The dispersed phase is added to the continuous fluid phase in a ratio of about 1:20 to about 1:2, dispersed to continuous phase (vol:vol) and preferably at a ratio of about 1:10 to about 1:5. The continuous fluid phase-dispersed phase is vigorously mixed in an inert atmosphere for a time, at a temperature, and at a speed adapted to achieve the desired final composite bead size. The final beads are sieved and dried. The final bead size ranges from about 25 to 800 um. Beads in size ranges of 75 to 150 um and from 150 to 300 um are preferred. Typically, the ratio of the diameter of the primary bead to that of the composite bead ranges from about 1:2.5 to 1:800; most typically the range is 1:75 to 1:200. Functional groups may be added to the final composite magnetic bead through further derivatization such as by the addition of amine groups using procedures taught by Merrifield et al., *Anal. Biochem.*, 117:147 (1981).

The following examples are given to illustrate the invention and should not be construed as limiting its scope.

EXAMPLES

Example 1
Preparation of high load paramagnetic composite beads
A continuous fluid phase is formed from water and polyvinyl alcohol. 600 grams of deionized water are weighed into a 1 Liter, 3 necked round-bottom flask fitted with a condenser, nitrogen inlet and an overhead stirrer (IKA). The flask is immersed in a water bath and the bath temperature set to 90° C. The water in the flask is purged with nitrogen from an air stone for 30 minutes. 6 grams of polyvinyl alcohol (Harco 26-88)(PVA) is added to the flask; the air stone is removed and a nitrogen blanket is maintained above the liquid surface for the duration of the reaction. The continuous fluid phase is stirred for 30 minutes at 90° C., then allowed to cool (with stirring) to 65° C. overnight. Separately, the dispersed phase is formulated from 0.15 grams of sodium nitrite ($NaNO_2$), 6 grams of primary hydrophobically coated paramagnetic beads, 70 grams of distilled styrene, 4.8 grams of divinyl benzene (63% divinyl content), 75 grams of diethyl benzene and 3 grams of benzoyl peroxide are mixed and degassed with nitrogen for 20 minutes. This mixture is poured into the continuous fluid phase, and the stirring speed adjusted to give droplets of the desired size (10–2000 micrometers). Reaction is allowed to proceed for 24 hours at 65° C. The reaction is then cooled, the particles are filtered. The product is washed with water to remove excess PVA and with tetrahydrofuran (THF) to remove unreacted monomer and inert diluents. The product was then dried and sieved.

Example 2
Preparation of High Load Chloromethyl Paramagnetic Particles.

400 grams of deionized water is weighed into a 1 Liter, 3 necked round-bottom flask fitted with a condenser, nitrogen inlet and an overhead stirrer (IKA). The flask is immersed in a water bath and the bath temperature set to 90° C. The water in the flask is purged with nitrogen from an air stone for 30 minutes. 2 grams of polyvinyl alcohol (Harco 26-88)(PVA) is added to the flask. The air stone is removed and a nitrogen blanket is maintained above the liquid surface for the duration of the reaction. The PVA mixture is stirred for 30 minutes at 90° C., then allowed to cool (with stirring) to 65° C. overnight. Separately, 0.1 grams of sodium nitrite ($NaNO_2$), 6 grams of primary hydrophobically coated paramagnetic beads, 53.4 grams of distilled styrene, 2.5 grams of divinyl benzene (63% divinyl content), 65 grams of diethyl benzene, 10.4 grams of chloromethylstyrene and 1 grams of benzoyl peroxide are mixed and degassed with nitrogen for 20 minutes. This mixture is poured into the PVA solution, and the stirring speed adjusted to give droplets of the desired size (10–2000 micrometers). Reaction is allowed to proceed for 24 hours at 65° C. The reaction is then cooled, the particles filtered and the product washed with water to remove excess PVA and with tetrahydrofuran (THF) to remove unreacted monomer and inert diluents. The product is then dried and sieved. Elemental analysis gave 3.41% chlorine (0.96 mmoles chlorine/gram of resin)

Example 3
Preparation of High Load Aminomethyl Paramagnetic Particles

To a 250 round bottom flask fitted with a condenser, nitrogen inlet and an overhead stirrer (IKA), was added 6 grams of chloromethyl paramagnetic beads prepared as in Example 2, 100 ml of dimethylformamide and 1.2 grams (6.4 mmole) potassium phthalimide and mixture stirred at 50° C. for 20 hours. At the end of 20 hours, the product was washed with dimethylformamide, methanol, water and ethanol and then dried under vacuum to provide phthalimide incorporated beads.

To 6 grams of phthalimide incorporated beads was added 200 ml of absolute ethanol and 2 ml of hydrazine monohydrate. The mixture was refluxed for 10 hours. The material was then filtered, washed with ethanol, aqueous sodium hydroxide, distilled water and ethanol in that order to give aminomethyl paramagnetic particles, dark black in color. Elemental analysis gave 2.01% nitrogen, 83.83% carbon, 7.10% hydrogen and 2.40% iron.

Example 4

Figure 1A:
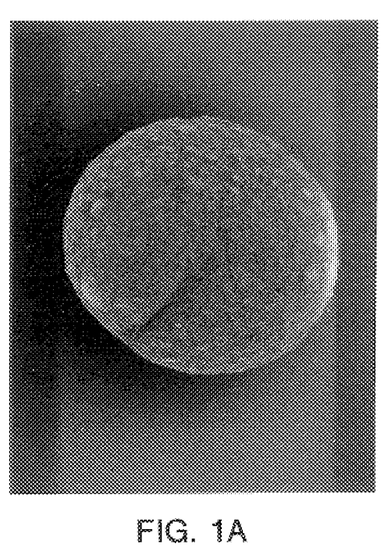
FIG. 1(a) is a scanning electron micrograph of chloromethyl paramagnetic derivatized polystyrene beads 1 at a solution of 150×.
Figure 1B:
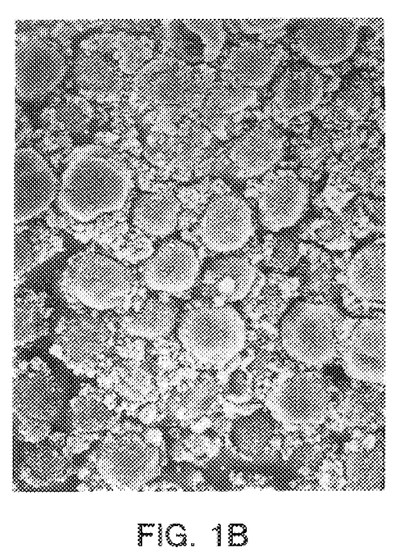
FIG. 1(b) is a scanning electron micrograph of a chloromethyl paramagnetic derivatized polystyrene bead 1 at a resolution of 6500×.
Figure 2A:
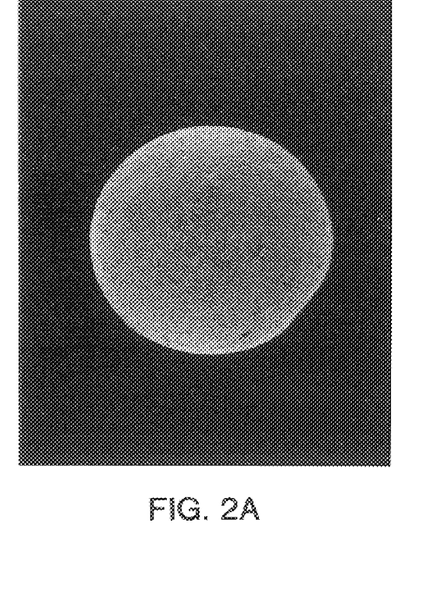
FIG. 2(a) is a scanning electron micrograph of polyethylene glycol derivatized polystyrene paramagnetic beads 3 at a resolution of 150×.
Figure 2B:
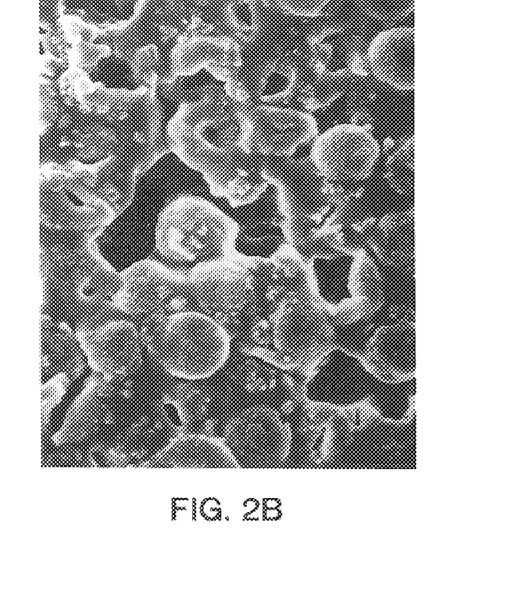
FIG. 2(b) is a scanning electron micrograph of a polyethylene glycol derivatized polystyrene paramagnetic bead 3 at a resolution of 6500×.

Composite magnetic beads from the batch used to provide the micrograph of FIG. 1, were suspended in various solvents and the following was observed. Beads expand in dimethyl formamide (DMF), methylene chloride, and tetrahydrofuran. See Table 1.

When the composite beads are suspended in DMF and allowed to remain in the solvent for 1 hr at 100° C. then exposed to a neodynium magnetic separator such as is available from Advanced Magnetics Lab., Cambridge, Mass., the composite beads are seen to remain intact. Small rigid polymeric coated magnetite particles which have become separated from the microporous matrix are not observed.

TABLE 1

Volume Changes of Composite Paramagnetic Beads (100 mg) Having An Average Diameter of 400 micrometers

| Solvent | Volume (ml) | Change in Volume (ml) | Floats/Sinks |
|---|---|---|---|
| none (dry) | 0.7 | — | — |
| DMF | 1.6 | 0.9 | sinks |
| water | 0.7 | 0 | floats |

The preferred starting material, polystyrene polymer coated bead described above, is available from Polymer Laboratories Ltd., Church Stretton, Shropshure, UK) Preferably, the starting material has a haloalkyl functionality covalently bound to the polystyrene matrix and has an average diameter of at least 0.2 millimeters to about 1.0 millimeters. Most preferably, the starting material has chloromethyl functionalities covalently linked to the polystyrene polymer matrix.

A spacer arm, (also termed an "arm") which is defined herein as a long chain hydrophilic molecule which will distance the binding site of a peptide or protein from the polystyrene coated bead, is covalently bound to the paramagnetic polystyrene bead at the haloalkyl functionality. The spacer arm is chosen from organic polymers which will provide a surface which is more hydrophilic than the polymer matrix surface itself. The increased surface hydrophilicity is thought to facilitate loading of the bead when the paramagnetic polystyrene bead is used as a support for organic synthesis of peptides and to reduce non-specific binding when the surface of the support is coupled to peptides or proteins for assay or therapeutic purposes. The spacer arm should have an average molecular weight of form at least about 500 to about 4,000 daltons. Exemplary spacer arm components would include polyalkylene glycol diamines such as polyethylene glycol (PEG), poly acrylimides, and carbohydrate molecules. It is preferred that a polyalkylene glycol diamine arm of about 1,500 to about 3,000 daltons be utilized. Most preferably due to its commercial availability, a 2,000 dalton polyethylene diamine known by the trademarked name of Jeffamine 2001 (available from Texaco Chemical Co., currently Huntsman Corporation of Austin, Tex.) is used. Surprisingly, it has been found that attachment of Jeffamine 2001 to the polystyrene chloromethyl functionalities can be directly and efficiently achieved with sonication and heat in the presence of excess spacer arm such as polyalkylene glycol diamine. A ten fold excess of spacer arm relative to the amount of beads present is preferred. However, the concentration of the spacer arm component can range between 5 to 50 equivalents by weight of the support material.

Prior to use, the paramagnetic polystyrene beads with attached spacer arms are coupled with a lower molecular weight linker which provides a functional group for covalent bonding of an amino acid or of a terminal amino acid of a protein to the support through the spacer arm. Examples of such linkers include (p-[(R,S)-a-(9H-Fluoren-9-yl)-methoxyformamido]-2,4-dimethoxybenzyl]-phenoxyacetic acid (available form Calbiochem-Novabiochem, La Jolla, Calif. and Advanced Chemtech Louisville, Ky.), also known as Rink amide linker; 4-hydroxymethyl benzoic acid linker; 4-(4-hydroxymethyl-3-methoxyphenoxy)-butyric acid linker; and 3-(4-hydroxymethylphenoxy)-propionic acid linker. Attachment of the linker to a polyakylene glycol spacer arm is through the formation of an amide bond. Once attached, each linker can provide a free hydroxymethyl group that is used to form an ester bond with an amino acid. When the bead is to be used for peptide or protein synthesis, it is preferred that the linker have an acid cleavable site proximal to the ester bond and that the amino acid binding site be protected during coupling to the spacer arm. It is also preferred that a 9-fluorenylmethoxycarbonyl (Fmoc) group be utilized to protect the alkylamine site on the linker prior to amino acid coupling. However, other groups such as tert-butyl carbamate (tBoc) may be substituted for the Fmoc group. When the bead is to be used in immunoassays as a coupled support for a bound ligand or antibody, an acid cleavable linker is not required. However, a free carboxylic group should be provided. It is preferred that sulfosuccinimidyl-4-(N-maleimidomethyl) cyclohexane-1-carboxylate (available from Pierce, Rockford, Ill.) be utilized as the linker, although the spacer arm may be reacted with succinic anhydride or maleic anhydride to yield a linker with a free carboxylic acid group.

Peptide synthesis utilizing the inventive bead is initiated by deprotecting the alkylamine site on the linker. An amino acid having a protected reactive site is then coupled to the linker alkylamine site. As with the linker the protective group may be any protective group known in the art, however a Fmoc group is preferred due to the commercial availability of amino acids having such a protected site. Unreacted material is separated from the Fmoc-amino acid-linker-spacer arm-bead by applying a magnet to the side of the reaction vessel and siphoning off the solution. Washing is performed in a similar manner. Additional amino acids are added by first deprotecting the site where addition will occur, then coupling the protected amino acid thereto as before. The amino acids may be naturally occurring or may be the mirror image of naturally occurring amino acids or may be derivatives of either of the aforementioned. The peptide may include repeat sequences of amino acids or may consist of a chain of a single amino acid or may be a random sequence of amino acids. Once the desired peptide or protein is achieved, the terminal amino acid is deprotected, and then the peptide is acid cleaved from the linker at the aminoalkyl site on the linker. Acid cleaving is preferably accomplished using trifluoroacetic acid in methylene chloride. However, hydrochloric acid in ether or trifluoromethanesulfonic acid in ether may be used.

Experimental Section

Materials. Diisopropylethylamine (DIEA) was distilled from ninhydrin under reduced pressure. UV spectrophotometry was carried out using a Milton Roy 1001+ spectrophotometer. $^1$H NMR was carried out using a Bruker AMX300 spectrometer. Magnetic separation was accomplished with the use of a BioMag Separator from Advanced Magnetics, Cambridge, Mass. Sonication was accomplished using a (Heat Systems Inc.; Farmingdale, N.Y.) sonicator model XL2020.

General Magnetic Separation Procedure. A BioMag Separator was applied to the side of the reaction vessel resulting in the beads adhering to the side. The solvent was then siphoned off. The BioMag Separator was removed and fresh solvent added and the mixture shaken. This process was repeated with each wash.

Example 1

Attachment of Jeffamine 2001 to Chloromethylated Magnetic Beads 1 to give Polyethylene Glycol Bound Magnetic Beads 3. To a round bottom flask was added 2.0 grams of chloromethylated magnetic beads 1 (having a substitution of 0.96 mmoles chlorine/gram of support and a average particle diameter of 0.4–0.5 millimeters) and 20 grams of Jeffamine 2001 and 30 mL of dimethylformamide (DMF) and mixture sonicated using a Heat Systems Sonicator for a total of 8 hours then heated at 60° C. for a total of 15 hours. The solid was then filtered and washed repeatedly with DMF, methanol (MeOH), water ($H_2O$) and methylene chloride ($CH_2Cl_2$). The resin was placed under a vacuum for 8 hours to give 3.9 grams of 3 as dark brown beads with an average particle diameter of 0.4–0.5 mmeters (Scheme 1). Nitrogen elemental analysis gave a loading of 0.47 mmoles of Nitrogen/gram of resin (0.24 mmoles Jeffamine/gram of resin). Chlorine elemental analysis showed less than 0.05% chlorine remaining.

Example 3

Coupling and Deprotection of Rink Amide Linker (6). To 1.0 grams Jeffamine containing paramagnetic beads 3 was added 1.5 grams (2.88 mmole) of PyBop (Benzotriazole-1-yl-oxy-tris-pyrolidino-phosphonium hexafluorophosphate obtained from Novabiochem) and 1.5 grams (2.77 mmole) of Rink amide linker 4(p-[(R,S)-a-(9H-Fluoren-9-yl)-methoxyformamido]-2,4-dimethoxybenzyl]-phenoxyacetic acid; available from Calbiochem-Novabiochem; La Jolla, Calif. and Advanced Chemtech, Louisville, Ky.) dissolved in 10 mL of DMF. The mixture was then rotated at room temperature using a LabQuake shaker (Scientific Products, McGaw Park, Ill.) for 24 hours. The mixture was then filtered and washed with DMF (4x), MeOH (3x), DMF (2x), MeOH (2x) and methylene chloride (4x) in that order. The solid was placed under pump vacuum to give 0.95 grams of the 9-fluorenylmethoxcarbonyl (Fmoc) protected, rink amide magnetic beads 5 (Scheme 2). The level of substitution was determined by a Fmoc spectrophotometric assay according to the method of Green, J. and Bradley, K., Tetrahedron, 49:4141 (1993) and was found to be 0.16 mmole Fmoc/gram.

To 0.5 grams (0.08 mmole) of Fmoc protected magnetic beads 5 was added 10 mL of 50% piperidine in dimethylformamide (DMF) and the mixture was shaken for 30 minutes. The beads were separated and washed with DMF Scheme 1

Example 2

Comparison Of Swelling Properties of Polyethylene Glycol Bound Support 3 vs. Untreated Beads 1. 100 mg of both Polyethylene Glycol Bound support 3 and untreated support 1 were added to separate graduated volumetric centrifuge tubes and their dry volumes recorded. To the beads were then added $H_2O$ and mixtures rotated for 24 hours and the bead volumes were again recorded. This was repeated again with fresh batches of beads with the exception that dimethylformamide was used as the solvent. The results in Table 1 show enhanced swelling and wetting properties in water which are indicative of the increased hydrophilicity of the inventive bead.

TABLE 1

| Beads (100 mg)/<br>Solvent | Volume (ml) | Change in Volume<br>(ml)<br>(solvent-dry) | Floats/Sinks |
|---|---|---|---|
| untreated (1)/dry | 0.7 | — | — |
| untreated (1)/DMF | 1.6 | 0.9 | sinks |
| untreated (1)/$H_2O$ | 0.7 | 0 | floats |
| treated (3)/dry | 0.4 | — | — |
| treated (3)/DMF | 1.1 | 0.7 | sinks |
| treated (3)/$H_2O$ | 0.6 | 0.2 | sinks |

(3x), methanol (3x), $CH_2Cl_2$ (1x) and DMF (1x), following the general magnetic separation procedure to give 6 (Scheme 2).

Example 4

Solid-phase Synthesis of Dipeptide Ac-Gly-Ala-$NH_2$ off Magnetic Beads (6). To the deprotected support 6 (0.08 mmole)) was added a solution of 0.15 grams (0.48 mmole) of Fmoc-Ala in 5 mL of DMF, 0.25 grams (0.48 mmole) of PyBop in 5 mL of DMF, 0.1 mL (0.57 mmole) of diisopropylethylamine (DIEA) mixture rotated for 2 hours. The support was washed with DMF (3x), methanol (3x), $CH_2Cl_2$ (1x) and DMF (2x) following the general magnetic separation procedure. The support was then deprotected using 10 mL of 50% piperidine in DMF for 30 minutes. Coupling and deprotection of Fmoc-Gly, was accomplished in the same manner with the washes being done following the general magnetic separation procedure. To the deprotected glycine bound support was added 0.25 mL of DIEA and 0.25 mL of acetic anhydride; then the mixture was rotated for 2 hours. After 2 hours, the beads were washed and separated following the previous protocol to give 7 (Scheme 2) after drying under pump vacuum.

Example 5

Cleavage of Dipeptide Ac-Gly-Ala-NH$_2$ off Magnetic Beads (7). To the dried beads 7 was added 10 mL of a 10% trifluoroacetic acid (TFA) in methylene chloride and mixture shaken for 2 hours. The beads were magnetically separated from the mother liquid, then the mother liquor was siphoned off. Another 10 mL of 10% TFA—CH$_2$Cl$_2$ solution was added to the beads and the mixture was shaken for 5 minutes. The beads were magnetically separated from the mother liquid. The mother liquor was siphoned off and combined with the previous acid wash. The volatile components were removed under reduced pressure to give an oil. The oil was precipitated from diethyl ether to give 7 mg of 8 as a white powder. $^1$H NMR (d-DMSO) δ 1.1–1.3 (m, 3H), 1.85 (s, 3H), 3.6–3.7 (m, 2H), 4.1–4.3 (m, 1H), 7.0 (br s, 1H), 7.2 (br s, 1H), 7.8–8.0 (m, 1H), 8.1–8.2 (m, 1H); chemical ionization-MS (M+H)=188 and (M+NH$_4$) 205.

Example 6

Scanning Electron Microscopy Study Comparing Wet Polyethylene Glycol Bound Paramagnetic Support 3 vs. Wet Untreated Support 1. Both Beads 1 and 3 were mounted on to stubs and lightly coated with gold-palladium. Their surface characteristics were studied using scanning electron microscopy (see FIG. 1 & FIG. 2).

Example 7

Reduction of Antibody Molecules. About 1 to 5 mg of intact antibody (IgG) (available from Pierce; Rockford, Ill.) may be dissolved in 2 mL of 0.1M sodium phosphate, 0.15M NaCl, 5 mM EDTA, pH 6.0. To this solution may be added 12 mg of 2-mercaptoethylamine. After the mixture is incubated at 37° C. for 1.5 hours, a crude reduced antibody can be obtained. This reduced antibody may be desalted using a 15-mL Sephadex G-25 column equilibrated with 50 mM Tris, 0.15M NaCl, 5 mM EDTA, pH 8.5

Example 8
Coupling of Jeffamine Paramagnetic Beads to Reduced Antibody Molecules. Ten Jeffamine paramagnetic beads incorporating a terminal alkylamine functionality such as those obtained from the process illustrated in Example 4, may be prepared for coupling to the reduced antibody (IgG) of Example 7 by a washing the beads with water and then with ice cold buffer ("buffer"), 4° C., containing 0.2M sodium phosphate, 0.15M NaCl, pH 7.2. To this bead mixture is then added 43.6 mg of sulfosuccinimidyl-4-(N-maleimidomethyl)cyclohexane-1-carboxylate (available from Pierce; Rockford, Ill.). the mixture is then rotated for 1hour at 4° C., then overnight at room temperature. After rotation, the beads should be washed first with buffer, then with a 1M NaCl solution, then again with buffer to remove unreacted starting materials. After immersion in a minimum of buffer, the beads may be coupled to the reduced antibody by gently rotating the reduced antibody and the beads overnight at room temperature. The final antibody-spacer arm-paramagnetic bead complex may be obtained by washing these beads with buffer, then with 1M NaCl, then with buffer.

The foregoing is considered only illustrative of the currently preferred embodiments of the invention presented herein. Since numerous modifications and changes will occur to those skilled in the art, it is not desired to limit the invention to the exact construction used to illustrate the various means comprising this invention.

What is claimed is:

1. A method of making a solid-phase support having a hydrophilic surface for magnetic separation of support bound components from unbound components, comprising the steps of:

providing a paramagnetic polymer bead comprised of a plurality of polystyrene coated metal oxide particles randomly dispersed in a polystyrene matrix, said polystyrene matrix comprised of a styrene monomer, wherein at least one said styrene monomer has a covalently bonded haloalkyl group;

adding an excess amount of a hydrophilic polymer having a molecular weight of between at least about 400 to 4,000 daltons; and sonicating said hydrophilic polymer with said paramagnetic polymer bead to obtain a paramagnetic-polystyrene-spacer arm bead.

2. The method of claim 1 wherein the hydrophilic polymer is selected from the group consisting of a polyalkylene glycol diamine, a polyacrylimide, and a carbohydrate.

3. The method of claim 2 wherein said hydrophilic polymer has a terminal amine.

4. The method of claim 3 wherein said excess amount of said hydrophilic polymer is about 5 to about 25 fold relative to that of said paramagnetic polymer bead.

5. The method of claim 4 further including the step of reacting said terminal amine group with an amide linker having a protected group.

6. The method of claim 5 wherein said protected group is Fmoc.

7. The method of claim 6 wherein said amide linker is p-[(R,S)-a-(9H-Fluoren-9-yl)-methoxyformamido]-2,4-dimethoxybenzyl]-phenoxyacetic acid.

8. The method of claim 2 further including the step of reacting said hydrophilic polymer with a low molecular weight organic anhydride to provide a carboxylate group.

9. The method of claim 8 wherein anhydride is selected from the group consisting of succinic anhydride and maleic anhydride.

10. The method of claim 8 further including the steps of: providing a reduced antibody and coupling said reduced antibody to said carboxylate group.

11. The method of claim 8 wherein said reduced antibody is desalted prior to coupling.

12. A method for synthesizing a peptide or a protein comprising the steps of:

a.) providing a paramagnetic polymer bead comprised of a plurality of polystyrene coated metal oxide particles randomly dispersed in a polystyrene matrix, said polystyrene matrix comprised of a styrene monomer, wherein at least one said styrene monomer has a covalently bonded haloalkyl group;

b.) sonicating a hydrophilic polymer having a terminal amine group and a molecular weight of between at least about 400 to 4,000 daltons with said paramagnetic polymer bead to obtain a paramagnetic-polystyrene-spacer arm bead;

c.) forming an amide bond between said paramagnetic-polystyrene-spacer arm bead and a linker to provide a paramagnetic-polystyrene-spacer arm-linker bead;

d.) esterifying said paramagnetic-polystyrene-spacer arm-linker to a first amino acid having a protected amine group;

e.) deprotecting said protected amine group to provide a reactive amine site;

f.) coupling a second amino acid having a protected amine group to said reactive amine site; and g.) sequentially repeating steps e and f until a peptide is obtained.

13. The method of claim 12 further including the step of acid cleaving said peptide from said paramagnetic-polystyrene-spacer arm-linker bead.

14. The method of claim 12 wherein said first amino acid either differs from or is the same as said second amino acid.

15. The method of claim 13 further including the step of deprotecting said linker prior to step d.

16. A paramagnetic solid-phase support having a hydrophilic surface for magnetic separation of support bound components from unbound components, said support comprising:

a paramagnetic polymer bead comprised of a plurality of polystyrene coated metal oxide particles randomly dispersed in a polystyrene matrix, said polystyrene matrix comprised of a styrene monomer, wherein at least one said styrene monomer has a haloalkyl group which is covalently bonded to said styrene monomer;

a spacer arm, said spacer arm forming an amide bond with said haloalkyl group; and a linker having a free carboxylic acid terminal end, said linker forming an outer most surface on said bead.

17. The paramagnetic solid phase support of claim 16 wherein said spacer arm is selected from the group consisting of polyalkylene glycol diamines and poly acrylimides.

18. The paramagnetic solid phase support of claim 17 wherein said linker is selected from the group consisting of (p-[(R,S)-a-(9H-fluoren-9-yl)-methoxyformamido]-2,4-dimethoxybenzyl]-phenoxyacetic acid linker; 4-hydroxymethyl benzoic acid linker; 4-(4-hydroxymethyl-3-methoxyphenoxy)-butyric acid linker; 3-(4-hydroxymethylphenoxy)-propionic acid linker.

19. The paramagnetic solid phase support of claim 18 wherein said linker has a protected reactive site.

20. The paramagnetic solid phase support of claim 16 wherein said spacer arm is a carbohydrate and said linker is sulfosuccinimidyl-4-(N-maleimidomethyl) cyclohexane-1-carboxylate.

* * * * *